United States Patent [19]

Lutz et al.

[11] 4,066,441

[45] Jan. 3, 1978

[54] PREEMERGENCE HERBICIDAL METHODS AND COMPOSITIONS USING 2,6-DINITROXYLIDINE COMPOUNDS

[75] Inventors: Albert William Lutz, Montgomery Township, Somerset County; Robert Eugene Diehl, Trenton, both of N.J.

[73] Assignee: American Cyanamid Company, Stamford, Conn.

[21] Appl. No.: 538,980

[22] Filed: Jan. 6, 1975

Related U.S. Application Data

[60] Division of Ser. No. 323,000, Jan. 12, 1973, Pat. No. 3,920,742, which is a continuation-in-part of Ser. No. 262,807, June 14, 1972, abandoned, which is a continuation-in-part of Ser. No. 174,938, Aug. 25, 1971, abandoned.

[51] Int. Cl.² ............................................... A01N 9/20
[52] U.S. Cl. ...................................................... 71/121
[58] Field of Search ......................................... 71/121

[56] References Cited

U.S. PATENT DOCUMENTS

| | | | |
|---|---|---|---|
| 3,227,758 | 1/1966 | Richter et al. | 71/121 |
| 3,530,184 | 9/1970 | Minieri et al. | 71/121 |
| 3,576,618 | 4/1971 | Samuel | 71/121 |
| 3,764,624 | 10/1973 | Strong et al. | 71/121 |
| 3,895,934 | 7/1975 | Linder | 71/121 |

FOREIGN PATENT DOCUMENTS

| | | | |
|---|---|---|---|
| 43-5028 | 2/1968 | Japan | 71/121 |

OTHER PUBLICATIONS

Kupelian, "Plant Growth–Regulating 2,6-dinitroanilines" (1973) CA78 No. 84010z, (1973).

*Primary Examiner*—Glennon H. Hollrah
*Attorney, Agent, or Firm*—Robert P. Raymond

[57] ABSTRACT

This invention relates to certain novel preemergence herbicidal methods and compositions employing substituted 2,6-dinitroaniline compounds.

8 Claims, No Drawings

PREEMERGENCE HERBICIDAL METHODS AND COMPOSITIONS USING 2,6-DINITROXYLIDINE COMPOUNDS

This is a division of application Ser. No. 323,000 filed Jan. 12, 1973; now U.S. Pat. No. 3,920,742 granted Nov. 18, 1975; which in turn, is a continuation-in-part of application Ser. No. 262,807, filed June 14, 1972 now abandoned, which is in turn a continuation-in-part of application Ser. No. 174,938, filed Aug. 25, 1971 now abandoned.

This invention relates to certain novel preemergence herbicidal methods and compositions employing substituted 2,6-dinitroaniline compounds.

The novel 2,6-dinitroaniline compounds of the present invention may be represented by the following structural formula:

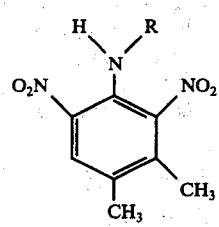

wherein,

R represents 1-ethylbutyl; 1-ethylpropyl; 1-methylpropyl or 1-methylbutyl.

The above-identified compounds are highly effective herbicidal agents.

The herbicidal methods of the present invention comprise application of a herbicidally effective amount of one or more compounds of Formula I to the soil containing the seeds of undesirable plant species to be controlled.

Wherein an asymmetric carbon atom exists in the dinitroaniline compounds above, optical isomerism may exist. Accordingly, such compounds may be employed as separate antimers or in admixture, as in a racemic composition. Unless there is indication to the contrary by reference to such a compound, the unresolved composition is intended herein. Separation of antimers, where desired, may be effected by convention resolution techniques. A convenient method relates to the introduction of an optically active substituent, such as a (—)-sec-butylamino group into the ring system, as by nucleophilic substitution, as exemplified below.

Preferably, application of these compounds, or active ingredients is made using the herbicidal compositions described below with conventional application methods.

The 2,6-dinitroaniline compounds are prepared by a nucleophilic substitution of a 1-substituent, such as, a chloro group, with the appropriately substituted amine. While chloro is a preferred substituent, and the discussion is in terms thereof other conventional equivalent substituents, such as bromo or iodo are included herein. The displacement may be conducted with or without an organic solvent, such as toluene, benzene or preferably xylene.

The reaction, which is graphically illustrated below, is carried out by heating the reactants, preferably between 50° C. and 150° C.

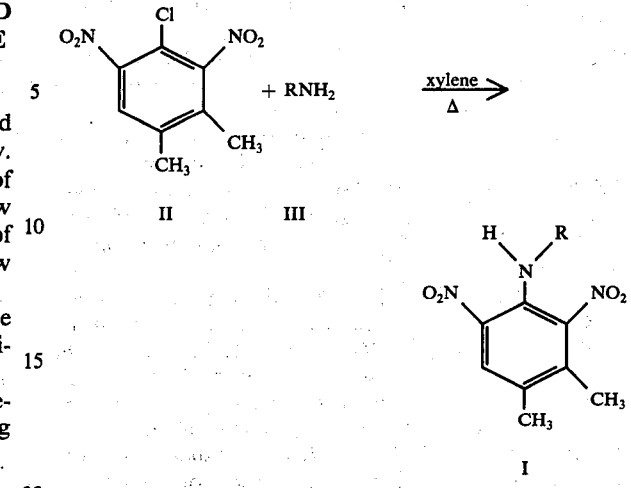

wherein R is as defined above.

The chlorobenzene intermediate can be prepared by reacting an appropriately substituted aniline with ethyl chloroformate in benzene at about 10° C. to 50° C. to yield the correspondingly substituted N-(ethoxycarbonyl)-3,4-substituted aniline. This product is then treated with a cold solution of sulfuric and nitric acid, i.e., at about 0° C. to 20° C. to obtain the N-(ethoxycarbonyl)-3,4-disubstituted-2,6-dinitroaniline. Reaction of the thus-formed product with sulfuric acid at an elevated temperature, preferably between about 100° C. and 150° C., converts the N-(ethoxycarbonyl) product to the 3,4-disubstituted-2,6-dinitroaniline. The amino group is replaced by a chlorine atom by first heating the compound with glacial acetic acid and diazotizing the amine with a mixture of sodium nitrite in sulfuric acid. This is followed by treating the diazotized mixture with a mixture of cuprous chloride in hydrochloric acid, and then heating the thus-formed mixture to about 40° C. to 80° C. to obtain the chlorinated compound.

The chlorinated intermediate can also be prepared by reacting a mixture of fuming sulfuric acid and fuming nitric acid with 4-chloro-o-xylene at about 10° C. to 60° C., pouring the mixture over ice and separating the precipitated solid. Recrystallization of the solid from methanol or other lower alkyl alcohol $C_1$–$C_4$ yields the high purity product.

The preemergence herbicidal compositions of the present invention are solid or liquid formulations comprising an effective amount of one or more of the 2,6-dinitroaniline compounds of Formula I, with a herbicidal adjuvant, i.e., an inert carrier or other conventional formulation aid.

Preparation of said compositions broadly involves admixing an effective amount of the herbicidal agent and adjuvant.

Use of said compositions broadly involves application of an effective amount of said compounds or preferably said compositions to the soil containing seeds of the plants to be controlled.

Typical formulations include, for example, dusts, dust concentrates, wettable powders, granulars, and the like. Application by conventional methods and equipment is usually made at rates of from about ½ pound per acre to about 20 pounds per acre and preferably ¼ to 8 pounds per acre of active material.

Dusts are generally prepared by grinding together from about 1 to 15% by weight of the active material with from about 99 to 85% by weight of a solid diluent, such as an attaclay, kaolin, diatomaceous earth, fullers earth, talc, pumice or the like.

Dust concentrates are prepared in similar fashion to the dusts excepting that generally about 15 to about 95% by weight of active material is used.

Granular formulations may be prepared by applying a liquid solution of the active material to sorptive granular carriers, such as attaclay, kaolin, or diatomite granules. Alternatively, they may be mixed with inert carriers and applied to non-sorptive granules, such as sand or limestone.

Wettable powders are prepared by grinding the active ingredient with a solid carrier, such as used in the dust formulations. Usually, about 25 to 75% by weight of the active material and from about 73 to 23% by weight of solid carrier is used. In addition, there is generally added about 1% to 5% by weight of a dispersing agent, such as alkali metal salts of naphthalene sulfuric acid and anionic-nonionic blends, and from about 1 to 5% by weight of a surfactant, such as polyoxyethylene alcohols, acids, adducts, sorbitan fatty acid esters and sorbitol esters. Typical formulations by weight percent are given below.

TABLE I

Typical Wettable Powder Formulations

| A | Ingredients |
|---|---|
| 25% | 3,4-dimethyl-2,6-dinitro-N-3-pentylaniline |
| 65% | attaclay |
| 5% | sodium lignosulfonate |
| 5% | sodium N-methyl-N-oleoyl taurate |

| B | Ingredients |
|---|---|
| 33% | N-sec-butyl-3,4-dimethyl-2,6-dinitroaniline |
| 59% | attaclay |
| 5% | sodium lignosulfonate |
| 3% | alkyl phenoxy polyoxyethylene ethanol |

The wettable powder formulations are usually dispersed in water and applied as a liquid spray to the area or locus where control of undesirable plant species is desired.

For use as preemergence herbicides, the dusts or liquid sprays containing the active compound can be applied to the soil shortly after planting or they may be incorporated into the soil by the technique referred to as preplant incorporation.

The practice and advantages of the present invention and preparation of the active ingredients used therein is further illustrated by the following examples which are not to be taken as being limitative thereof. Parts and percentages herein are by weight unless otherwise indicated.

EXAMPLE 1

Preparation of 3,4-Dimethyl-2,6-dinitrochlorobenzene

Two grams of 3,4-dimethyl-2,6-dinitroaniline [Chemical Abstracts 44: 4447 (1950)] is dissolved in 40 ml. of warm glacial acetic acid. The solution is cooled to room temperature and a mixture of 0.9 grams of sodium nitrite in 7 ml. of concentrated sulfuric acid is added very slowly leaving a solid in the mixture. This mixture is then added to a solution of cuprous chloride in concentrated hydrochloric acid. The cuprous chloride solution is prepared by dissolving 3.24 grams of $CuSO_4 \cdot 5H_2O$ in water and adding NaCl to the warm solution. While holding the blue solution in an ice bath, a solution of 1.24 grams of sodium meta-bisulfite and 0.52 grams of NaOH in 12 ml. of water is added. A white precipitate forms and is dissolved in 12 ml. of concentrated hydrochloric acid. The diazonium mixture is then warmed, filtered, and the solid collected and recrystallized from cyclohexane. The product has a melting point of 109° C. to 111° C. The procedures are repeated using 16 grams of the amine, yielding 11 grams of product, having a melting point of 111° C. to 113° C.

EXAMPLE 2

Preparation of 3,4-Dimethyl-2,6-dinitrochlorobenzene

Fuming sulfuric acid (750 ml., 23%) and fuming nitric acid (240 ml., 90%) are mixed at 0° C. to 45° C. Then 4-chloro-o-xylene (270 grams, 1.93 moles) is added at 10° C. to 60° C. When the addition is complete, the reaction mixture is poured into 8000 ml. of ice and 4000 ml. water and then filtered. The cake is washed with 4000 ml. of water, 500 ml. methanol, and finally 500 ml. of petroleum ether. The cake is then slurried two times with 200 ml. xylene and filtered. The filter cake is then washed with 50 ml. cold xylene and 300 ml. of methanol at 50° C. The solid is then recrystallized from 2500 ml. of methanol and washed with 2 pints of petroleum ether. The yield of white solid is 120 grams with melting point 112° C. to 113° C.

EXAMPLE 3

Preparation of N-sec-Butyl-3,4-dimethyl-2,6-dinitroaniline

A mixture of 4-chloro-3,5-dinitro-o-xylene (140 grams, 0.61 mole), mono-sec-butylamine (184 ml., 1.82 moles), and xylene (1400 ml.) is brought to reflux. After refluxing overnight, the reaction mixture is cooled and filtered. The precipitate is washed with petroleum ether. The filtrate and washings are combined, washed with 500 ml. of 10% hydrochloric acid, and finally with 2 liters of water. The organic layer is separated and dried. Removal of the drying agent and the solvent leaves an orange oil which crystallizes with the addition of petroleum ether. A yellow orange solid (150.6 grams, 86.5%) with melting point 42° C. to 43° C. is collected.

EXAMPLES 4 to 7

Following the general procedures of Example 3, substituting the appropriate amine for the amine used therein, yields products having the following formula and properties set forth in Table II below.

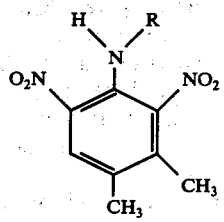

IV

TABLE II

| Example Number | Substituents R | Melting Point °C | Crystallizing Solvent |
|---|---|---|---|
| 4 | CH—C$_3$H$_7$-n<br>\|<br>C$_2$H$_5$ | 40–42 | |
| 5 | CHC$_2$H$_5$<br>\|<br>CH$_3$ | 43–44 | hexane |
| 6 | CH(C$_2$H$_5$)$_2$ | 56–57 | methanol |

TABLE II-continued

| Example Number | Substituents R | Melting Point °C | Crystallizing Solvent |
|---|---|---|---|
| 7 | CHCH$_2$CH$_2$CH$_3$<br>\|<br>CH$_3$ | 42–43 | methanol |

EXAMPLE 8

Preparation of (−)-N-sec-Butyl-2,6-dinitro-3,4-xylidine (−)-sec-Butylamine [prepared according to L. Verbit and P. J. Heffron, *Journal of Organic Chemistry* 32, 3199 (1967)] was reacted with 4-chloro-3,5-dinitro-o-xylene as by the general procedure of Example 3 to give a yellow-orange solid with melting point 37° C. to 38.5° C., $[\alpha]_D^{25°} = -51.38°$ (c 2.071, ethanol). Concentrations, abbreviated c herein, are measured in grams per 100 ml. of solution.

EXAMPLES 9 to 10

Preparation of (−)-N-[1-(Methoxymethyl)propyl]-2,6-dinitro-3,4-xylidine (−)-2-Amino-1-butanol [100 grams, prepared according to D. Pitre and E. B. Grabitz, *Chimia* 23, 399 (1969)] was added in a dropwise manner to a stirred solution of tert-butanol (800 ml.) containing potassium tert-butoxide (126 grams). After warming this mixture to 70° C. to 80° C. for 2 hours, methyl iodide (175 grams) was added slowly at temperatures below 50° C. The suspension which formed was then stirred with refluxing overnight. After removal of the solid phase by filtration, the filtrate was fractionally distilled to give (−)-1-(methoxymethyl)propylamine contaminated with traces of tert-butanol, boiling point 125° C. to 147° C./760 mm. This amine was then allowed to react with 4-chloro-3,5-dinitro-o-xylene, as described earlier, to give the desired product as a bright yellow solid with melting point 42.5° C. to 44° C., $[\alpha]_D^{25°} = -137.6°$ (c 2.504, chloroform).

The following optical isomers were also prepared using the appropriate optically active amine and following essentially the procedure of above:

TABLE III

| Ex. No. | Compound Name | Melting Point °C | $[\alpha]_D^{25°}$ |
|---|---|---|---|
| 9 | (+)-N-sec-butyl-2,6-dinitro-3,4-xylidine | 38–38.5 | + 50.18<br>(c 2.217, ethanol) |

TABLE III-continued

| Ex. No. | Compound Name | Melting Point °C | $[\alpha]_D^{25°}$ |
|---|---|---|---|
| 10 | (−)-N(1-methylbutyl)-2,6-dinitro-3,4-xylidine | 59–61 | − 58.0<br>(c 2.449, ethanol) |

EXAMPLES 11 to 14

The selective preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous-acetone solution containing test compound in sufficient quantity to provide the equivalent of about 0.25 to 4 pounds per acre of test compound per cup. The treated cups are then placed on greenhouse benches, watered and cared for in accordance with conventional greenhouse procedures. Three or four weeks after treatment, the tests are terminated and each cup is examined and rated according to the rating system set forth below. The herbicidal proficiency of the active ingredients of the present invention is evident from the test results which are reported in the tables below.

| Rating System | |
|---|---|
| Rating System | % Difference in Growth from the Check* |
| 0— no effect | 0 |
| 1— possible effect | 1 - 10 |
| 2— slight effect | 11 - 25 |
| 3— moderate effect | 26 - 40 |
| 5— definite injury | 41 - 60 |
| 6— herbicidal effect | 61 - 75 |
| 7— good herbicidal effect | 76 - 90 |
| 8— approaching complete kill | 91 - 99 |
| 9— complete kill | 100 |
| 4— abnormal growth, i.e., a definite physiological malformation but with an over-all effect less than a 5 on the rating scale. | |

*Based on visual determination of stand, size, vigor, chlorosis, growth malformation and over-all plant appearance.

| Plant Abbreviations | |
|---|---|
| CR— Crabgrass | BA— Barnyard grass |
| VEL— Velvet leaf | FOX— Green foxtail |
| PI— Pigweed | MG— Annual Morning-glory |
| LA— Lambsquarters | COT— Cotton |
| COR— Corn | SB— Sugarbeets |
| WO— Wild oats | SOY— Soybean |

TABLE IV

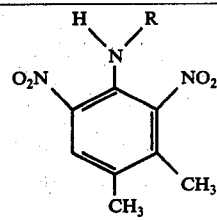

| Ex. No. | R | Rate lb./acre | CR | VEL | PI | LA | COR | WO | BA | FOX | MG | COT | SB | SCY |
|---|---|---|---|---|---|---|---|---|---|---|---|---|---|---|
| 11 | C$_2$H$_5$CHCH$_2$CH$_2$CH$_3$ | 4 | 9 | 7 | 9 | 8 | 5 | 5 | 9 | 9 | 6 | 0 | 8 | 0 |
| | | 2 | 9 | 7 | 8 | 8 | 0 | 3 | 8 | 9 | 2 | 0 | 8 | 0 |
| | | 1 | 9 | 5 | 8 | 8 | 0 | 1 | 8 | 9 | 0 | 0 | 6 | 0 |
| | | ½ | 9 | 2 | 6 | 8 | 0 | 1 | 6 | 8 | 0 | 0 | 2 | 0 |
| | | ¼ | 8 | 0 | 5 | 7 | 0 | 0 | 5 | 6 | 0 | 0 | 0 | 0 |

TABLE IV-continued

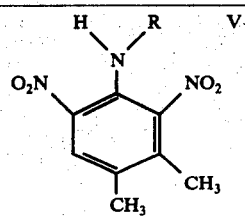

| Ex. No. | R | Rate lb./acre | \multicolumn{12}{c|}{Species - Greenhouse Soil} |
|---|---|---|---|---|---|---|---|---|---|---|---|---|---|---|
| | | | CR | VEL | PI | LA | COR | WO | BA | FOX | MG | COT | SB | SCY |
| 12 | CH₃CH—CH₂CH₃ | 4 | 9 | 8 | 8 | 8 | 3 | 2 | 9 | 9 | 2 | 0 | 8 | 3 |
| | | 2 | 9 | 8 | 8 | 8 | 3 | 0 | 9 | 9 | 0 | 0 | 8 | 0 |
| | | 1 | 9 | 5 | 7 | 8 | 0 | 0 | 9 | 9 | 0 | 0 | 7 | 0 |
| | | ½ | 9 | 0 | 3 | 7 | 0 | 0 | 7 | 0 | 0 | 0 | 0 | 0 |
| | | ¼ | 8 | 0 | 0 | 5 | 0 | 0 | 5 | 5 | 0 | 0 | 0 | 0 |
| 13 | C₂H₅CHC₂H₅ | 4 | 9 | 7 | 8 | 8 | 7 | 5 | 9 | 9 | 7 | 5 | 5 | 3 |
| | | 2 | 9 | 7 | 8 | 8 | 6 | 2 | 9 | 9 | 7 | 2 | 5 | 2 |
| | | 1 | 9 | 6 | 7 | 8 | 2 | 0 | 7 | 9 | 6 | 1 | 2 | 0 |
| | | ½ | 9 | 5 | 6 | 8 | 1 | 0 | 8 | 9 | 3 | 0 | 1 | 0 |
| | | ¼ | 9 | 5 | 6 | 7 | — | 0 | 5 | 9 | 1 | 0 | 0 | 0 |
| 14 | CH₃CHC₃H₇ | 4 | 9 | 7 | 8 | 8 | 8 | 3 | 9 | 9 | 5 | 0 | 6 | 0 |
| | | 2 | 9 | 2 | 8 | 8 | 2 | 2 | 9 | 9 | 6 | 0 | 5 | 0 |
| | | 1 | 9 | 2 | 8 | 8 | 0 | 0 | 8 | 9 | 5 | 9 | 2 | 0 |
| | | ½ | 9 | 0 | 5 | 7 | 0 | 0 | 3 | 8 | 2 | 6 | 0 | 0 |
| | | ¼ | 9 | 1 | 2 | 6 | 0 | 0 | 2 | 5 | 0 | 0 | 0 | 0 |

EXAMPLES 15 to 19

The herbicidal activity of various compounds of the present invention are demonstrated by the following tests, wherein seeds of monocotyledonous and dicotyledonous plants are planted in the top half-inch of soil in small plastic pots and sprayed with a solution of test compound. All spray applications are made to a dry soil surface through nozzles designed to deliver 86 gallons per acre of spray solution. Immediately after treatment, the pots are labeled, moved to a greenhouse, and watered. Three weeks after treatment, the herbicide activity is recorded using the Herbicidal Activity rating system reported below.

From the data reported in the table below, it can be seen that (1) the racemic compounds are highly active herbicidal agents; (2) the dextrorotatory (+) isomers are less active than the racemic compounds, but still effective as herbicidal agents at higher rates of application; and (3) the levorotatory (−) isomers are much more effective as herbicidal agents than either the corresponding racemic compound or the corresponding dextrorotatory (+) isomer.

| \multicolumn{3}{c|}{Species List} |
|---|---|---|
| Code | Common Name | Scientific Name |
| LA | Lambsquarters | Chenopodium album |

-continued

| \multicolumn{3}{c|}{Species List} |
|---|---|---|
| Code | Common Name | Scientific Name |
| PI | Pigweed | Amaranthus retroflexus |
| MG | Morning-glory | Ipomoca hederacea |
| BA | Barnyard grass | Echinochloa crusgalli |
| CR | Crab grass | Digitairia sanguinalis |
| FO | Green foxtail | Setaria viridis |
| WO | Wild oat | Avena fatua |
| CN | Corn | Zea mays |
| CO | Cotton | Gossypium hirsuium |
| SY | Soybean | Glycine max |
| SB | Sugar beet | Beta vulgaris |
| VL | Velvet leaf | Abutilen theophrasti |

| \multicolumn{3}{c|}{Herbicidal Activity Index} |
|---|---|---|
| Rating Scale | Observation | *% Difference in Growth from Charts |
| 9 | Complete kill | 100 |
| 8 | Approaching complete kill | 91 – 99 |
| 7 | Good herbicidal effect | 70 – 90 |
| 6 | Herbicidal effect | 61 – 75 |
| 5 | Definite injury | 41 – 60 |
| 4 | (See Below) | — |
| 3 | Moderate effect | 26 – 40 |
| 2 | Slight effect | 11 – 25 |
| 1 | Possible effect | 1 – 10 |
| 0 | No effect | 0 |

4 — Reserved for abnormal plant growth, i.e. a definite physiological malformation but with an over-all effect of less than 5 on the rating scale.
*Based on visual determination of stand, size, vigor, chlorosis.

TABLE V

Herbicidal Activity of Optically Active and Racemic Dinitroaniline Compounds

| Ex. No. | Compound | Rate lb./Acre | \multicolumn{12}{c|}{Test Species} |
|---|---|---|---|---|---|---|---|---|---|---|---|---|---|---|
| | | | LA | PI | MG | BA | CR | FO | WO | CN | CO | SY | CB | VL |
| 15 | [structure: NO₂ / NH—CH—C₂H₅ / NO₂ / CH₃ / CH₃ with CH₃ (−)] | 1 | 8 | 8 | 0 | 8 | 9 | 9 | 0 | 0 | 2 | 3 | 3 | 7 |
| | | 1/2 | 7 | 8 | 0 | 8 | 8 | 9 | 0 | 0 | 0 | 0 | 3 | 6 |
| | | 1/4 | 5 | 7 | 0 | 2 | 8 | 8 | 0 | 0 | 0 | 0 | 0 | 0 |
| | | 1/8 | 3 | 6 | 0 | 6 | 6 | 8 | 0 | 0 | 0 | 0 | 0 | 0 |
| | | 1/16 | 1 | 5 | 0 | 2 | 0 | 7 | 0 | 0 | 0 | 0 | 0 | 0 |

TABLE V-continued
Herbicidal Activity of Optically Active and Racemic Dinitroaniline Compounds

| Ex. No. | Compound | Rate lb./Acre | LA | PI | MG | BA | CR | FO | WO | CN | CO | SY | CB | VL |
|---|---|---|---|---|---|---|---|---|---|---|---|---|---|---|
| 16 | NO₂-C₆H₂(NH-CH(CH₃)-C₂H₅)(NO₂)(CH₃)(CH₃) (±) | 1 | 8 | 7 | 0 | 8 | 9 | 9 | 0 | 0 | 3 | 2 | 0 | 0 |
|  |  | 1/2 | 8 | 7 | 0 | 9 | 9 | 9 | 0 | 0 | 0 | 0 | 0 | 0 |
|  |  | 1/4 | 7 | 6 | 0 | 2 | 8 | 8 | 0 | 0 | 0 | 0 | 0 | 0 |
|  |  | 1/8 | 0 | 0 | 0 | 0 | 6 | 8 | 3 | 0 | 0 | 0 | 0 | 0 |
|  |  | 1/16 | 0 | 0 | 0 | 0 | 3 | 7 | 0 | 0 | 0 | 0 | 0 | 0 |
| 17 | NO₂-C₆H₂(NH-CH(CH₃)-C₂H₅)(NO₂)(CH₃)(CH₃) (+) | 1 | 3 | 5 | 0 | 8 | 8 | 8 | 0 | 3 | 2 | 0 | 0 | 0 |
|  |  | 1/2 | 3 | 0 | 0 | 7 | 2 | 8 | 0 | 0 | 0 | 3 | 0 | 0 |
|  |  | 1/4 | 1 | 0 | 0 | 7 | 0 | 7 | 0 | 0 | 0 | 0 | 0 | 0 |
|  |  | 1/8 | 0 | 0 | 0 | 3 | 0 | 1 | 0 | 0 | 0 | 0 | 0 | 0 |
|  |  | 1/16 | 0 | 0 | 0 | 0 | 0 | 0 | 0 | 0 | 0 | 0 | 0 | 0 |
| 18 | O₂N-C₆H₂(HN-CHCH₂CH₂CH₃)(NO₂)(CH₃)(CH₃) (−) | 2 | 8 | 9 | 2 | 9 | 9 | 8 | 2 | 3 | 0 | 0 | 7 | 6 |
|  |  | 1 | 8 | 8 | 3 | 8 | 9 | 8 | 3 | 2 | 0 | 0 | 3 | 5 |
|  |  | 1/2 | 8 | 8 | 0 | 8 | 9 | 8 | 0 | 0 | 0 | 0 | 0 | 0 |
|  |  | 1/4 | 7 | 7 | 0 | 8 | 9 | 8 | 0 | 0 | 0 | 0 | 0 | 0 |
|  |  | 1/8 | 5 | 5 | 0 | 7 | 8 | 7 | 0 | 0 | 0 | 0 | 0 | 0 |
| 19 | O₂N-C₆H₂(HN-CHCH₂CH₂CH₃)(NO₂)(CH₃)(CH₃) (±) | 2 | 8 | 8 | 0 | 8 | 9 | 7 | 7 | 4 | 0 | 0 | 7 | 6 |
|  |  | 1 | 8 | 8 | 0 | 8 | 9 | 9 | 5 | 0 | 0 | 0 | 3 | 5 |
|  |  | 1/2 | 7 | 7 | 0 | 8 | 8 | 8 | 3 | 0 | 0 | 0 | 0 | 0 |
|  |  | 1/4 | 7 | 5 | 0 | 7 | 8 | 8 | 0 | 0 | 0 | 0 | 0 | 0 |
|  |  | 1/8 | 3 | 3 | 0 | 3 | 8 | 5 | 0 | 0 | 0 | 0 | 0 | 0 |

We claim:
1. A method for the preemergence control of undesirable plant species comprising applying to soil containing seeds of said undesirable plant species a herbicidally effective amount of a compound of the formula:

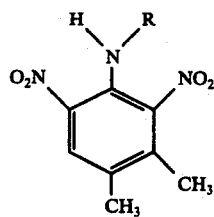

wherein R represents 1-ethylbutyl; 1-ethylpropyl; 1-methylpropyl or 1-methylbutyl.

2. A preemergence herbicidal composition comprising an admixture of a inert herbicidal adjuvant and a herbicidally effective amount of a compound of the formula:

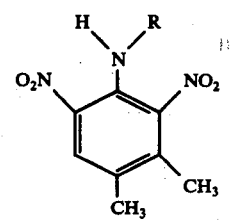

wherein R represents 1-ethylbutyl; 1-ethylpropyl; 1-methylpropyl or 1-methylbutyl.

3. A composition according to claim 2 wherein the compound is: N-sec-butyl-2,6-dinitro-3,4-xylidine.

4. A composition according to claim 2 wherein the compound is: N-(1-ethylpropyl)-2,6-dinitro-3,4-xylidine.

5. A method for the preemergence control of undesirable plant species comprising applying to soil containing seeds of said undesirable plant species a herbicidally effective amount of a compound of the formula:

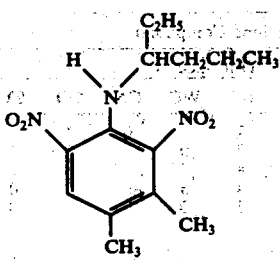

6. A method for the preemergence control of undesirable plant species comprising applying to soil containing seeds of said undesirable plant species a herbicidally effective amount of a compound of the formula:

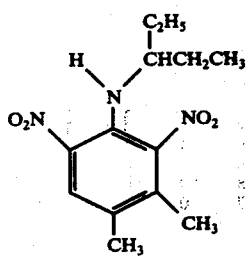

7. A method for the preemergence control of undesirable plant species comprising applying to soil containing seeds of said undesirable plant species a herbicidally effective amount of a compound of the formula:

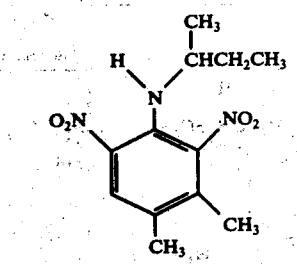

8. A method for the preemergence control of undesirable plant species comprising applying to soil containing seeds of said undesirable plant species a herbicidally effective amount of a compound of the formula:

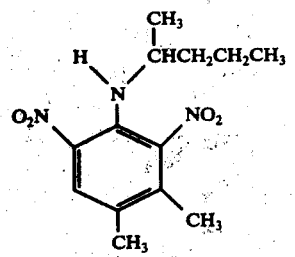

* * * * *